(12) United States Patent
Woollam et al.

(10) Patent No.: US 6,937,341 B1
(45) Date of Patent: Aug. 30, 2005

(54) SYSTEM AND METHOD ENABLING SIMULTANEOUS INVESTIGATION OF SAMPLE WITH TWO BEAMS OF ELECTROMAGNETIC RADIATION

(75) Inventors: John A. Woollam, Lincoln, NE (US); Galen L. Pfeiffer, Lincoln, NE (US); Daniel W. Thompson, Lincoln, NE (US); Blaine D. Johs, Lincoln, NE (US); Craig M. Herzinger, Lincoln, NE (US)

(73) Assignee: J. A. Woollam Co. Inc., Lincoln, NE (US)

( * ) Notice: Subject to any disclaimer, the term of this patent is extended or adjusted under 35 U.S.C. 154(b) by 399 days.

(21) Appl. No.: 10/238,241

(22) Filed: Sep. 10, 2002

Related U.S. Application Data

(63) Continuation-in-part of application No. 09/756,515, filed on Jan. 9, 2001, now Pat. No. 6,455,853, and a continuation-in-part of application No. 09/419,794, filed on Oct. 18, 1999, now Pat. No. 6,549,282, and a continuation-in-part of application No. 09/162,217, filed on Sep. 29, 1998, now Pat. No. 6,034,777.

(60) Provisional application No. 60/318,518, filed on Sep. 10, 2001, provisional application No. 60/183,977, filed on Feb. 22, 2000.

(51) Int. Cl.[7] ............................ G01J 4/00; G01N 21/00
(52) U.S. Cl. ........................ 356/436; 356/440; 356/364
(58) Field of Search ................................ 356/364–369, 356/436, 246, 72–73, 445

(56) References Cited

U.S. PATENT DOCUMENTS

| | | | |
|---|---|---|---|
| 4,076,420 A | 2/1978 | De Maeyer et al. ........... 356/73 |
| 4,159,874 A | 7/1979 | Dearth et al. ................. 356/73 |
| 4,472,633 A | 9/1984 | Motooka ...................... 250/338 |
| 4,807,994 A | 2/1989 | Felch et al. .................. 356/326 |
| 4,810,658 A * | 3/1989 | Shanks et al. ............... 356/246 |
| 5,172,182 A * | 12/1992 | Sting et al. .................. 356/246 |
| 5,313,264 A | 5/1994 | Ivarsson et al. .............. 356/73 |
| 5,329,357 A | 7/1994 | Bernoux et al. ............. 356/369 |
| 5,373,359 A | 12/1994 | Woollam et al. ............. 356/328 |
| 5,486,701 A | 1/1996 | Norton et al. ............... 250/372 |
| 5,504,582 A | 4/1996 | Johs et al. ................... 356/369 |
| 5,521,706 A | 5/1996 | Green et al. ................. 356/369 |
| 5,582,646 A | 12/1996 | Woollam et al. ............. 118/708 |
| 5,625,455 A | 4/1997 | Nash et al. .................. 356/369 |
| 5,666,201 A | 9/1997 | Johs et al. ................... 356/369 |
| 5,706,212 A | 1/1998 | Thompson et al. .......... 364/525 |
| 5,757,494 A | 5/1998 | Green et al. ................. 356/369 |
| 5,872,630 A | 2/1999 | Johs et al. ................... 356/369 |

(Continued)

OTHER PUBLICATIONS

An articl by Johs, titled "Regression Calibration Method For Rotating Element Ellipsometers", which appeared in Thin Film Solids, vol. 234 in 1993.

(Continued)

Primary Examiner—Zandra V. Smith
(74) Attorney, Agent, or Firm—James D. Welch

(57) ABSTRACT

Disclosed are system and method for characterizing a system consisting of a fluid sample on a two sided stage, utilizing data obtained by applying, from both sides thereof, beams of electromagnetic radiation to a fluid coated surface in a containing cell volume. The beams can have the same or different wavelength content and/or polarization state, and can be applied at the same or different magnitude angles-of-incidence, and a third typically unpolarized beam can be applied at a normal angle-of-incidence.

40 Claims, 5 Drawing Sheets

U.S. PATENT DOCUMENTS

| | | | |
|---|---|---|---|
| 5,900,633 A | 5/1999 | Solomon et al. | 250/339.08 |
| 5,923,031 A * | 7/1999 | Naya | 356/244 |
| 5,926,284 A * | 7/1999 | Naya et al. | 356/445 |
| 5,991,048 A | 11/1999 | Karlson et al. | 356/445 |
| 6,034,777 A | 3/2000 | Johs et al. | 356/369 |
| 6,049,220 A | 4/2000 | Borden et al. | 324/765 |
| 6,200,814 B1 | 3/2001 | Malmqvist et al. | 436/52 |
| 6,316,274 B1 | 11/2001 | Herron et al. | 436/518 |
| 6,417,925 B1 * | 7/2002 | Naya | 356/445 |
| 2002/0024668 A1 | 2/2002 | Stehle et al. | 356/369 |
| 2004/0142482 A1 * | 7/2004 | Westphal et al. | 436/164 |

OTHER PUBLICATIONS

A paper by Nijs & Silfhout, titled "Systematic and Random Errors in Rotating-Analyzer Ellipsometry", J. Opt. Soc. Am. A., vol. 5, No. 6, (Jun. 1988).

An article by Jellison Jr. titled "Data Analysis for Spectroscopic Ellipsometry", Thin Film Solids, 234, (1993).

"Unified Analysis of Ellipsometry Errors Due to Imperfect Components Cell-Window Birefringence, and Incorrect Azimuth Angles", J. of the Opt. Soc. Am., vol. 61, No. 5, (May 1971).

"Analysis of Systematic Errors in Rotating-Analyzer Ellipsometers", J. of the Opt. Soc. Am., vol. 64, No. 11, (Nov. 1974).

An unpublished article by Poksinski et al. titled Total Internal Reflection Ellipsometry, describes application of total internal reflection to investigate protein using ellipsometric techniques.

A paper by Straaher et al., titled "The Influence of Cell Window Imperfections on the Calibration and Measured Data of Two Types of Rotating Analyzer Ellipsometers", Surface Sci., North Holland, 96, (1980).

An article by Collins titled "Automated Rotating Element Ellipsometers: Calibration, Operation, and Real-Time Applications", Rev. Sci. Instrum. 61(8), Aug. 1990.

An article by Kleim et al. titled "Systematic Errors in Rotating-Compensator Ellipsometry" published in J. Opt. Soc. Am./vol. 11, No. 9, Sep. 1994.

An Article by An and Collins titled "Waveform Analysis With Optical Multichannel Detectors: Applications for Rapid-Scan Spectroscopic Ellipsometer", Rev. Sci. Instrum., 62 (8), Aug. 1991.

A paper which is co-authored by the inventor herein is titled "In Situ Multi-Wavelength Ellipsometric Control of Thickness and Composition of Bragg Reflector Structures", by Herzinger, Johs, Reich, Carpenter & Van Hove, Mat. Res. Soc. Symp. Proc., vol. 406, 1996.

* cited by examiner

SYSTEM AND METHOD ENABLING SIMULTANEOUS INVESTIGATION OF SAMPLE WITH TWO BEAMS OF ELECTROMAGNETIC RADIATION

This application is a Continuation-In-Part of application Ser. No. 09/756,515 Filed Jan. 09, 2001 now U.S. Pat. No. 6,455,853, and therevia Claims benefit of Provisional Application Ser. No. 60/183,977 Filed Feb. 22, 2000. This application is further a Continuation-In-Part of Ser. No. 09/419, 794 filed Oct. 18, 1999 now U.S. Pat. No. 6,549,282 which CIP Ser. No. 09/162,217 filed Sep. 29, 1998 now U.S. Pat. No. 6,034,777 Filed Sep. 29, 1998 via Pending application Ser. No. 09/419,794 which depends from said 777 patent. This application further directly Claims Benefit of Provisional Application Ser. No. 60/318,518, Filed Sep. 10, 2001.

TECHNICAL FIELD

The disclosed invention relates to the use of reflectometer, spectrophotometer, polarimeter, ellipsometer and the like systems to investigate samples, and more particularly to a system which enables substantially simultaneous investigation of fluid, (liquid, film or solid), samples, such as biological samples, by at least two electromagnetic beams which are typically independently selected from wavelength ranges such as VUV, UV, Visible, Infrared, Far Infrared, and Radio Wave, and which are separately applied at separately selected angles-of-incidence.

BACKGROUND

The characterization of fluid samples, such as biological samples, is increasing in importance. Further, it is known to investigate a sample placed on a first surface of a sample stage element, which sample stage element presents with first and second, typically, but not necessarily substantially parallel surfaces, by utilizing an electromagnetic beam applied from said first surface side of said sample stage element such that said beam reflects from said sample into a detector. It is further known to independently investigate a sample placed on a sample stage element first surface utilizing an electromagnetic beam applied from a second, oppositely facing surface side of said sample stage element such that said beam reflects from the sample into a detector. Of course the sample stage element must be transparent to said electromagnetic radiation applied from the second surface side thereof in order to access the sample. Further, it is to be understood that electromagnetic radiation can be of any functional wavelength, either monochromatic, (ie. laser source), or spectroscopic.

The primary motivation for the disclosed invention is found in a need to do more definitive assays and analysis in areas such as:
   antibody/antigen interactions;
   microbiology (eg. viruses, toxins etc.);
   physiological (eg. hormones);
   drugs (therapeutic and illegal).

In addition, the present invention finds application in fundamental science where, for instance, bonding mechanisms and attachment rates for proteins and/or DNA to surfaces and other biomaterials are of interest.

The application of Spectroscopic Ellipsometry (SE) to biologics provides utility because reflectance from Bio-films on opaque substrates is difficult to detect where intensity changes are small. In addition Surface Plasmon Resonance (SPR), while sensitive, has a limited spectral range and can be applied only to limited types of substrate materials and layer thicknesses.

It is noted that a suitable system for investigating biologics must be relatively immune to such as temperature sensitive birefringence of electromagnetic wavelength windows, which requires careful design and mounting. In addition, temperature sensitivity of reagents and reactions and reagent concentration sensitivity can enter artifacts into results, hence a suitable system for investigating biologics must provide means to minimize random effects therein. A robust system and method therefore should provide compensation capability, at least to compensate the identified birefringence, during data in analysis.

Continuing, while the herein disclosed invention can be used in any material system investigation system such as Polarimeter, Reflectometer, Spectrophotometer and the like Systems, an important application is with Ellipsometer Systems, whether monochromatic or spectroscopic. It should therefore be understood that Ellipsometry involves acquisition of sample system characterizing data at single or multiple Wavelengths, and at one or more Angle(s)-of-Incidence (AOI) of a Beam of Electromagnetic Radiation to a surface of the sample system. Ellipsometry is generally well described in a great many publication, one such publication being a review paper by Collins, titled "Automatic Rotating Element Ellipsometers: Calibration, Operation and Real-Time Applications", Rev. Sci. Instrum., 61(8) (1990).

A typical goal in ellipsometry is to obtain, for each wavelength in, and angle of incidence of said beam of electromagnetic radiation caused to interact with a sample system, sample system characterizing PSI and DELTA values, where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$, caused by interaction with said sample system. This is expressed by:

$$\text{TAN}(\psi)e^{i(\Delta)} = r_s/r_p.$$

(Note the availability of the phase DELTA (Δ) data is a distinguishing factor between ellipsometry and reflectometry).

Continuing, Ellipsometer Systems generally include a source of a beam of electromagnetic radiation, a Polarizer, which serves to impose a state of polarization on a beam of electromagnetic radiation, a Stage for supporting a sample system, and an Analyzer which serves to select a polarization state in a beam of electromagnetic radiation after it has interacted with a material system, and passed it to a Detector System for analysis therein. As well, one or more Compensator(s) can be present and serve to affect a phase angle between orthogonal components of a polarized beam of electromagnetic radiation. A number of types of ellipsometer systems exist, such as those which include rotating elements and those which include modulation elements. Those including rotating elements include Rotating Polarizer (RP), Rotating Analyzer (RA) and Rotating Compensator (RC). A preferred embodiment is a Rotating Compensator Ellipsometer System because, it is noted, Rotating Compensator Ellipsometer Systems do not demonstrate "Dead-Spots" where obtaining data is difficult. They can read PSI and DELTA of a Material System over a full Range of Degrees with the only limitation being that if PSI becomes essentially zero (0.0), DELTA can not then be determined as there is not sufficient PSI Polar Vector Length to form the angle between the PSI Vector and an "X" axis. In comparison, Rotating Analyzer and Rotating Polarizer Ellipsometers have "Dead Spots" at DELTA's near 0.0 or 180 Degrees and Modulation Element Ellipsometers also have "Dead Spots" at PSI near 45 Degrees). The utility of Rotating Compensator Ellipsometer Systems should then be apparent. Another benefit provided by fixed Polarizer (P) and Analyzer (A) positions is that polarization state sensitivity to input and output optics during data acquisition is essentially non-existent. This enables relatively easy use of optic fibers, mirrors, lenses etc. for input/output.

Further, it is to be understood that causing a polarized beam of electromagnetic radiation to interact with a sample system generally causes change in the ratio of the intensities of orthogonal components thereof and/or the phase angle between said orthogonal components. The same is generally true for interaction between any system component and a polarized beam of electromagnetic radiation. In recognition of the need to isolate the effects of an investigated sample system from those caused by interaction between a beam of electromagnetic radiation and system components other than said sample system, (to enable accurate characterization of a sample system per se.), this Specification incorporates by reference the regression procedure of U.S. Pat. No. 5,872,630 to Johs et al. in that it describes simultaneous evaluation of sample characterizing parameters such as PSI and DELTA, as well system characterizing parameters, and this Specification also incorporates by reference the Vacuum Chamber Window Correction methodology of U.S. Pat. No. 6,034,777 to Johs et al. to account for phase shifts entered between orthogonal components of a beam of electromagnetic radiation, by disclosed invention system windows and/or beam entry elements.

A Published Patent Application of which the applicants are aware is U.S. 2002/0024668 by Stehle et al. This application discloses the use of two electromagentic beams applied orthogonally to a sample, and one electromagentic beam applied normally thereto through effective windows which are oriented parallel to the surface of the sample.

Other patents of which the Inventor is aware include U.S. Pat. No. 5,757,494 to Green et al., in which is taught a method for extending the range of Rotating Analyzer/Polarizer ellipsometer systems to allow measurement of DELTA'S near zero (0.0) and one-hundred-eighty (180) degrees. Said patent describes the presence of a window-like variable bi-refringent components which is added to a Rotating Analyzer/Polarizer ellipsometer system, and the application thereof during data acquisition, to enable the identified capability.

A patent to Thompson et al. U.S. Pat. No. 5,706,212 teaches a mathematical regression based double Fourier series ellipsometer calibration procedure for application, primarily, in calibrating ellipsometers system utilized in infrared wavelength range. Bi-refringent window-like compensators are described as present in the system thereof, and discussion of correlation of retardations entered by sequentially adjacent elements which do not rotate with respect to one another during data acquisition is described therein.

A patent to Woollam et al, U.S. Pat. No. 5,582,646 is disclosed as it describes obtaining ellipsometric data through windows in a vacuum chamber, utilizing other than a Brewster Angle of Incidence.

Patent to Woollam et al, U.S. Pat. No. 5,373,359, patent to Johs et al. U.S. Pat. No. 5,666,201 and patent to Green et al., U.S. Pat. No. 5,521,706, and patent to Johs et al., U.S. Pat. No. 5,504,582 are disclosed for general information as they pertain to Rotating Analyzer ellipsometer systems.

Patent to Bernoux et al., U.S. Pat. No. 5,329,357 is identified as it describes the use of optical fibers as input and output means in an ellipsometer system.

U.S. Pat. No. 5,991,048 To Karlson et al. describes a system for practicing Surface Plasmon Resonance in which a light pipe arrangement is present upon which can be situated a flow cell. Sample entered to the flow cell becomes situated on the upper surface of the light pipe and light entered to the light pipe interacts with it from below, then exists and enters a multi-element detector at various angles.

U.S. Pat. No. 6,316,274 B1 to Herron et al. describes a single light source system for practicing multi-analyte homogeneous flouro-immunoassays, via detecting of reflected and transmitted beams.

U.S. Pat. No. 5,313,264 to Ivarsson et al. describes a single light source system in which a light beam accesses a sample via a prism, (which can be semicircular in shape), and reflects into a detector.

U.S. Pat. No. 4,159,874 to Dearth et al. describes another single light source system which includes upper and lower sensors.

U.S. Pat. No. 6,200,814 B1 to Malmquist et al. describes a method and system for providing laminar flow over one or more discrete sensing areas.

U.S. Pat. No. 4,076,420 to De Maeyer et al. describes a system for investigating fast chemical reactions by optical detection of, for instance, absorbtion or fluorescence or scattered light, including detection of polarized light.

Patents identified during the preparation and prosecution of. Pending application Ser. No. 09/756,515, from which this application is a CIP are:

U.S. Pat. No. 5,486,701 to Norton et al.;
U.S. Pat. No. 5,900,633 to Solomon et al.;
U.S. Pat. No. 4,807,994 to Felch et al.;
U.S. Pat. No. 4,472,633 to Motooka;
U.S. Pat. No. 6,049,220 to Borden et al.

Scientific Articles are also identified as follows:

An article by Johs, titled "Regression Calibration Method For Rotating Element Ellipsometers", which appeared in Thin Film Solids, Vol. 234 in 1993 is also identified as it describes an approach to ellipsometer calibration.

Another paper, by Straaher et al., titled "The Influence of Cell Window Imperfections on the Calibration and Measured Data of Two Types of Rotating Analyzer Ellipsometers", Surface Sci., North Holland, 96, (1980), describes a graphical method for determining a plane of incidence in the presence of windows with small retardation.

An article by Collins titled "Automated Rotating Element Ellipsometers: Calibration, Operation, and Real-Time Applications", Rev. Sci. Instrum. 61(8), August 1990 is disclosed for the general insight to ellipsometer systems it provides.

An article by Kleim et al. titled "Systematic Errors in Rotating-Compensator Ellipsometry" published in J. Opt. Soc. Am./Vol. 11, No. 9, September 1994 is identified as it describes calibration of rotating compensator ellipsometers.

An Article by An and Collins titled "Waveform Analysis With Optical Multichannel Detectors: Applications for Rapid-Scan Spectroscopic Ellipsometer", Rev. Sci. Instrum., 62 (8), August 1991 is also identified as it discusses effects such as Detection System Error Characterization, Stray Light, Image Persistence etc., and calibration thereof.

A paper which is co-authored by the inventor herein is titled "In Situ Multi-Wavelength Ellipsometric Control of Thickness and Composition of Bragg Reflector Structures", by Herzinger, Johs, Reich, Carpenter & Van Hove, Mat. Res. Soc. Symp. Proc., Vol.406, (1996) is also disclosed.

A paper by Nijs & Silfhout, titled "Systematic and Random Errors in Rotating-Analyzer Ellipsometry", J. Opt. Soc. Am. A., Vol. 5, No. 6, (June 1988) is also identified.

An article by Jellison Jr. titled "Data Analysis for Spectroscopic Ellipsometry", Thin Film Solids, 234, (1993) is also disclosed.

Papers of interest in the area by Azzam & Bashara;

"Unified Analysis of Ellipsometry Errors Due to Imperfect Components Cell-Window Birefringence, and Incorrect Azimuth Angles", J. of the Opt. Soc. Am., Vol 61, No. 5, (May 1971);

"Analysis of Systematic Errors in Rotating-Analyzer Ellipsometers", J. of the Opt. Soc. Am., Vol. 64, No. 11, (November 1974).

An unpublished article by Poksinski et al. titled "Total Internal Reflection Ellipsometry, describes application of total internal reflection to investigate protein using ellipsometric techniques.

It is also mentioned that a book by Azzam and Bashara titled "Ellipsometry and Polarized light" North-Holland, 1977 is disclosed and incorporated herein by reference for general theory, as is a book which is authority regarding mathematical regression, (ie. a book titled Numerical Recipes in "C", 1988, Cambridge University Press.

Continuing, to obtain valid data from an Ellipsometer, it is necessary to calibrate it. For insight, as generally described in the 630 patent with focus on a method of calibrating a spectroscopic rotating compensator material system investigation system, a generalized method of calibrating a material system investigation system can comprise the steps of:

a. providing a material system investigation system comprising a source of a polychromatic beam of electromagnetic radiation, a polarizer, a stage for supporting a material system, an analyzer, a dispersive optics and at least one detector system which contains a multiplicity of detector elements, said material system investigation system optionally comprising at least one compensator(s) positioned at a location selected from the group consisting of:

before said stage for supporting a material system, and
after said stage for supporting a material system, and
both before and after said stage for supporting a material system;

such that when said material system investigation system is used to investigate a material system present on said stage for supporting a material system, at least one of said analyzer or polarizer or at least one of said at least one compensator(s) is/are caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said material system, pass through said analyzer and interact with said dispersive optics such that a multiplicity of essentially single wavelengths are caused to simultaneously enter a corresponding multiplicity of detector elements in said at least one detector system;

b. in conjunction with other steps, developing a mathematical model of said material system investigation system which comprises as calibration parameter variables such as polarizer azimuthal angle orientation, present material system PSI, present material system DELTA, compensator azimuthal angle orientation(s), matrix components of said compensator(s), analyzer azimuthal angle orientation, and angle of incidence changing system representations, which mathematical model is effectively a transfer function which enables calculation of electromagnetic beam intensity as a function of wavelength detected by a detector element, given intensity as a function of wavelength provided by said source of a polychromatic beam of electromagnetic radiation;

c. causing a polychromatic beam of electromagnetic radiation produced by said source of a polychromatic beam of electromagnetic radiation, to pass through said polarizer, interact with a material system caused to be in the path thereof, pass through said analyzer, and interact with said dispersive optics such that a multiplicity of essentially single wavelengths are caused to simultaneously enter a corresponding multiplicity of detector elements in said at least one detector system, with said polychromatic beam of electromagnetic radiation also being caused to pass through present compensator(s);

d. obtaining an at least two dimensional data set of intensity values vs. wavelength and a parameter selected from the group consisting of:

angle-of-incidence of said polychromatic beam of electromagnetic radiation with respect to a present material system, and azimuthal angle rotation of one element selected from the group consisting of:
said polarizer; and
said analyzer;
at least one of said at least one compensator(s);

while at least one selection from the group consisting of
said polarizer; and
said analyzer;
at least one of said at least one compensator(s);

is caused to continuously rotate;

e. performing a mathematical regression of said mathematical model onto said at least two dimensional data set, thereby evaluating calibration parameters in said mathematical model;

said regression based calibration procedure evaluated calibration parameters serving to compensate said mathematical model for non-achromatic characteristics and non-idealities of said compensator(s), and for azimuthal angles of said polarizer, analyzer and compensator(s).

Said method of calibrating a material system investigation system can further comprise including calibration parameters for detector element image persistence and read-out non-idealities in the mathematical model, and further evaluating said calibration parameters for detector element image persistence and read-out non-idealities in said regression procedure.

Said method of calibrating a material system investigation system can include, in the step of developing a calibration parameter containing mathematical model of said spectroscopic rotating compensator ellipsometer system, the steps of providing a matrix representation of each of said polarizer, present material system, said compensator(s), and said analyzer etc., and determining a mathematical transfer function relating electromagnetic beam intensity out to intensity in, as a function of wavelength, by multiplication of said matrices.

Said method of calibrating a material system investigation system can further comprise the step of parameterizing calibration parameters by representing variation as a function of a member of the group consisting of: (wavelength, angle-of-incidence of said polychromatic beam of electromagnetic radiation with respect to a present material system, and azimuthal angle orientation of one element selected from the group consisting of: (said polarizer and said analyzer)), by a parameter containing mathematical equation, said parameters being evaluated during said mathematical regression.

Said method of calibrating a material system investigation system can preferably specifically include selecting calibration parameters which are parameterized, (such as polarizer azimuthal angle orientation, compensator azimuthal angle orientation(s), matrix components of said compensator(s), and analyzer azimuthal angle orientation), each as a function of wavelength.

Said method of calibrating a spectroscopic rotating compensator material system investigation system can involve using a material system which is selected from the group consisting of: (open atmosphere with the spectroscopic rotating compensator material system investigation system being oriented in a "straight-through" configuration, and other than open atmosphere with the spectroscopic rotating compensator material system investigation system being oriented in a "material-present" configuration).

Continuing, it should also be appreciated that when ellipsometer system components/elements are sequentially located adjacent to one another and are stationary with respect to one another, an ellipsometer "sees" the sum total thereof as a composite single element. For instance, if a sample system is present between two elements of a present invention electromagnetic beam intercepting angle-of-incidence changing system, an ellipsometric investigation will provide a PSI and DELTA of the composite thereof. This is clearly not what is desired. In view of this it is presented that the methodology described in the 777 patent, which is focused in application to correcting for phase shifts between orthogonal components of a polarized electromagnetic beam caused by its passing through vacuum chamber input and output windows, can be applied to compensate the effects of the presence of an invention electromagnetic beam intercepting angle-of-incidence changing system, as well. As insight to what is taught in the 777 patent consider that in-situ application of ellipsometry to investigation of a sample system present in a vacuum chamber presents a challenge to users of ellipsometer systems in the form of providing a mathematical model for each of said input and output windows, and providing a method by which the effects of said windows can be separated from the effects of an investigated sample system. (Like a disclosed invention system, input and output windows in a vacuum chamber are structurally positioned by said vacuum chamber and are not rotatable with respect to a sample system present in said vacuum chamber in use, thus preventing breaking correlation between parameters in equations for sequentially adjacent input and output windows and an investigated sample system by an element rotation technique). While correlation of parameters in mathematical equations which describe the effects of groupings of elements, (such as a compensator and an optional element(s)), can be tolerable, correlation between parameters in the mathematical model of an investigated sample system and other elements in the ellipsometer system must be broken to allow obtaining accurate sample system representing PSI and DELTA values, emphasis added. That is to say that correlation between parameters in a equations in a mathematical model which describe the effects of a stationary compensator and a sequentially next window element, (eg. correlation between effects of elements c. and d. or between f. and g. identified above), on a beam of electromagnetic radiation might be tolerated to the extent that said correlation does not influence determination of sample system describing PSI and DELTA values, but the correlation between parameters in equations which describe the effects of ellipsometer system components (eg. a., b., c., d., f., g., h. and i. identified above), and equations which describe the effects of a present sample system (eg. element e. above), absolutely must be broken to allow the ellipsometer system to provide accurate PSI and DELTA values for said sample system.

The 777 patent describes a method of accurately evaluating parameters in parameterized equations in a mathematical model of a system of spatially separated input and output windows, as applied in an ellipsometry or polarimeter setting which can be applied to the disclosed invention. Said 777 patent parameterized equations enable, when parameters therein are properly evaluated, independent calculation of retardation entered by each of said input window and said output window between orthogonal components of a beam of electromagnetic radiation caused to pass through said input and output windows. (It is to be understood that at least one of said input and output windows is bi-refringent).

While not independently establishing Patentability, a method of accurately evaluating parameters in parameterized equations in a mathematical model of a system of spatially separated input and output windows, said parameterized equations enabling, when parameters therein are properly evaluated, independent calculation of retardation entered by each of said input output windows between orthogonal components of a beam of electromagnetic radiation caused to pass through said input and output windows, at least one of said input and output windows being bi-refringent, comprises, in a functional order, the steps of:

a. providing spatially separated input and output windows, at least one of which input and output windows demonstrates birefringence when a beam of electromagnetic radiation is caused to pass therethrough, and further providing a means for supporting a sample system positioned between said input and output windows;
   b. positioning an ellipsometer system source of electromagnetic radiation and an ellipsometer system detector system such that in use a beam of electromagnetic radiation provided by said source of electromagnetic radiation is caused to pass through said input window, interact with a sample, in a plane of incidence thereto, and exit through said output window and enter said detector system;
   c. providing a sample to said means for supporting a sample system, the composition of said sample system being sufficiently well known so that retardance entered thereby to a polarized beam of electromagnetic radiation of a given wavelength, which is caused to interact with said sample system in a plane of incidence thereto, can be accurately modeled mathematically by a parameterized equation which, when parameters therein are properly evaluated, allows calculation of retardance entered thereby between orthogonal components of a beam of electromagnetic radiation caused to interact therewith in a plane of incidence thereto;
   d. in conjunction with other steps, providing a mathematical model for said ellipsometer system and said input and output windows, which comprises separate parameterized equations for independently calculating retardance entered between orthogonal components of a beam of electromagnetic radiation caused to pass through each of said input and output windows; such that where parameters in said mathematical model are properly evaluated, retardance entered between orthogonal components of a beam of electromagnetic radiation which passes through each of said input and output window, and further interacts with said sample system in a plane of incidence thereto can be independently calculated from said parameterized equations;

e. obtaining a spectroscopic set of ellipsometric data with said parameterizable sample system present on the means for supporting a sample system, utilizing a beam of electromagnetic radiation provided by said source of electromagnetic radiation, said beam of electromagnetic radiation being caused to pass through said input window, interact with said parameterizable sample system in a plane of incidence thereto, and exit through said output window;

f. by utilizing said mathematical model provided in step d. and said spectroscopic set of ellipsometric data obtained in step e., simultaneously evaluating parameters in said mathematical model parameterized equations for independently calculating retardance entered between orthogonal components in a beam of electromagnetic radiation caused to pass through said input window, interact with said sample in a plane of incidence thereto, and exit through said output window;

to the end that application of said parameterized equations for each of said input and output window and sample for which values of parameters therein have been determined in step f., enables independent calculation of retardance entered between orthogonal components of a beam of electromagnetic radiation by each of said input and output windows, and said sample system, at given wavelengths in said spectroscopic set of ellipsometric data, said calculated retardance values for each of said input window, output window and sample system being essentially uncorrelated.

Said method preferably, in step f., involves simultaneous evaluation of parameters in said mathematical model parameterized equations for said parameterizable sample, and for said input and output windows, and is achieved by a square error reducing mathematical curve fitting procedure.

Further, said method, in step d., involves provision of a mathematical model for said ellipsometer system and said input and output windows parameterizable sample, can involve, for each of said input and output windows, providing separate parameterized mathematical model equations for retardance entered to each of said two orthogonal components of a beam of electromagnetic radiation caused to pass through said input and output windows; at least one of said orthogonal components for each of said input and output electromagnetic beam intercepting angle-of-incidence changing systems being directed out of the plane of incidence of said electromagnetic beam onto said parameterizable sample system; such that calculation of retardation entered between orthogonal components of said beam of electromagnetic radiation, by said input window is provided by comparison of retardance entered to each of said orthogonal components for said input window, and such that calculation of retardation entered between orthogonal components of said beam of electromagnetic radiation, by said output window is provided by comparison of retardance entered to each of said orthogonal components for said output window.

Said method, in step f., provides for simultaneous evaluation of parameters in said mathematical model parameterized equations for said parameterizable sample system, and for said input and output windows, is preferably achieved by a square error reducing mathematical curve fitting procedure.

Said method, in step b., provides for positioning of an ellipsometer system source of electromagnetic radiation and an ellipsometer system detector system and typically includes positioning a polarizer between said source of electromagnetic radiation and said input window, and the positioning of an analyzer between said output window and said detector system, and the step e. obtaining of a spectroscopic set of ellipsometric data typically involves obtaining data at a plurality of settings of at least one component selected from the group consisting of:

said analyzer; and said polarizer.

Said method, in the step of providing mathematical model parameterized equations for enabling independent calculation of retardance entered by said input and said output window and a sample system between orthogonal components of a beam of electromagnetic radiation, can involve use of parameterized equations having a form selected from the group consisting of:

$ret(\lambda)=K1+(K2/\lambda)+(K3/\lambda);$ $ret(\lambda)=(K1/\lambda)$ $ret(\lambda)=(K1/\lambda)*(1+(K2/\lambda))$ $ret(\lambda)=(K1/\lambda)*(1+(K2/\lambda)+(K3/\lambda)).$ As the present application is a CIP from Pending application Ser. No. 09/756,515, it is also disclosed that the basic method disclosed therein enables quantifying thickness and impurity profile defining parameters in impurity profile containing membranes, via a method comprising the steps of providing an ellipsometer system, and sequentially or simultaneously obtaining ellipsometric data sets from both first and second sides of an impurity profile containing membrane, and providing a mathematical model of said impurity profile defining parameters comprising membrane thickness and impurity profile defining parameters, then performing a mathematical regression of said mathematical model onto data obtained from said impurity profile containing membrane by a selection from the group consisting of:

utilizing the data sets obtained from front and back of the thin membrane simultaneously;

utilizing the data sets obtained from front and back of the thin membrane independently; and utilizing the data sets obtained from front and back of the thin membrane both independently and simultaneously;

to evaluate said membrane thickness and impurity profile defining parameters. The concept of obtaining data from both sides of a sample, simultaneously or sequentially, and utilizing said data obtained simultaneously or independently to characterize the sample is thus established by said 515 application, and as regards the present invention, the "impurity profile defining parameters" in the 515 application can be considered analogically similar to the fluid sample atop a two sided stage in the present application.

Even in view of the prior art, there is identified a remaining need for a system which allows essentially simultaneous investigation of a sample, particularly a biological fluid sample, with two wavelengths, one wavelength being caused to approach from one side of the sample, and the second wavelength being caused to approach said sample from the second side thereof.

DISCLOSURE OF THE INVENTION

As disclosed in Pending application Ser. No. 09/756,515 Filed Jan. 9, 2001 with Priority back to at least Feb. 22, 2000, and of which this application is a CIP, the concept of simultaneously utilizing data obtained from investigating both sides of a thin solid sample with electromagnetic beams in analysis thereof, has proven utility. The invention disclosed herein builds on that basic concept and enables investigation of a fluid sample present on a surface, (eg. one side of a two sided sample stage element (STG)), with multiple beams, either alternatingly, simultaneously or at times separated by only a short time delay, without any need to alter system or sample configuration. One beam is applied directly to the sample, (the side of a sample stage element which provides the surface upon which is present the sample), and a second beam is applied from the opposite side, (eg. through said two sided sample stage element). Preferably a first electromagnetic beam is entered through an input window of a cell which is situated on a sample stage element surface upon which is the sample, and another beam is entered from the opposite side of the sample stage element through, for instance, a Prism or Semi-Spherical or Half-cylinder shaped beam entry element present adjacent thereto, however, alike shaped beam entry and exit means can be present on both sides of the sample stage element. For both said beams, the electromagnetic radiation is applied at a substantially normal angle of incidence at entry and exit locations of the cell windows or surface(s) of a Prism or Semi-Spherical or Half-Cylinder shaped beam entry element. Note that said two identified beams typically have a polarization state imposed thereupon and are each caused to approach said sample at oblique angles to said sample surface, which oblique angles can be of the same or different magnitudes with respect to the surface. It is to be understood that a third beam, typically non-polarized, can also be caused to approach said sample surface along a substantially normal locus thereto and enter through a third effective window.

The beam entry element can be made of ZnSe, Ge or Si, (with specific tradename examples being KRS-5, and INTRAN), to provide Infrared transparency, with the cell windows being transparent to UV, Visible and Near Infrared.

A disclosed system for enabling substantially simultaneous investigation of a fluid sample with at least two electromagnetic radiation beams comprises a sample stage element having a first surface, and a second surface, typically, but not necessarily substantially parallel to said first surface. Said system further comprises a cell adjacent to said first sample stage element surface which comprises:
  input and output windows;
  input and output means for entering and exiting fluid sample;
  an internal volume which is substantially closed but which has an opening adjacent to said sample stage element first surface such that fluid sample entered into said cell via said input means can access said adjacent sample stage surface.

Said system further comprises a beam entry element in functional combination with said sample stage element second surface.

In use fluid sample is entered to said cell through said input means for entering fluid sample, and one electromagnetic radiation beam is entered through said input window of said cell which is adjacent to one surface of the sample stage element, and a second electromagnetic radiation beam is entered through said beam entry element adjacent to said sample stage element second surface;

such that all entering and exiting electromagnetic radiation preferably enters and exits through window or beam entry element surfaces which are oriented substantially normal to the locus thereof.

It is noted that the beam entry element through which said second electromagnetic radiation beam is entered is preferably of a shape selected from the group consisting of:
  prism;
  semi-spherical; and
  half-cylinder;

and made of a material with is substantially transparent to said second beam contained wavelengths.

In addition, the cell can be separated from said sample stage first surface by "O" ring means, such that fluid sample entered into said cell becomes present within said "O" ring means on said sample stage first surface.

It should also be understood that at least two elements selected from the group:
  sample stage element;
  cell; and
  beam entry element;

can be integrated into one another. For instance, the cell can be continuous with the first surface of the sample stage element, and/or the sample stage element and the beam entry element can be of a continuous construction.

An "integrated" system for enabling substantially simultaneous investigation of a fluid sample with at least two electromagnetic radiation beams can then be described as comprising a cell with effective input and output windows; input and output means for entering and exiting fluid sample and an internal volume, said integrated system further comprising a beam entry element in functional combination with said cell, and located therebelow, as the integrated system is viewed in upright side elevation. In use fluid sample is entered to said cell through said input means for entering fluid sample, and one electromagnetic radiation beam is entered through said effective input window of said cell, and a second electromagnetic radiation beam is entered through said beam entry element. As before, all entering and exiting electromagnetic radiation preferably enters and exits through effective cell window or beam entry element surface(s) which are oriented substantially normal to the locus thereof. And, again, the effective input and output windows and the beam entry element, through which electromagnetic radiation beams are passed can be of a shape selected from the group consisting of:
  prism;
  semi-spherical; and
  half-cylinder.

The input and output windows can also be of separate construction. Further, in one variation the cell and beam entry element are of continuous construction.

Another recitation of a presently disclosed system for enabling substantially simultaneous investigation of a fluid sample with at least two electromagnetic radiation beams provides that said system comprise a cell, which cell comprises:
  effective input and output windows;
  input and output means for entering and exiting fluid sample;
  an internal volume presenting with a surface therewithin.

Said system further comprises a beam entry element in functional combination with said cell, and being located, as viewed in upright side elevation, below said surface within said cell. In use fluid sample is entered to the internal volume of said cell through said input means for entering fluid sample, and one electromagnetic radiation beam is entered through said effective input window of said cell, and a second electromagnetic radiation beam is entered through said beam entry element, to the end that both said first and second electromagnetic beams interact, at the same or different magnitude oblique angles with respect to said surface in said internal volume of said cell, with said fluid sample present on said surface, and then exit and enter detector means.

Further, in any embodiment, the cell can also comprise a third window and a third electromagnetic beam can be caused to enter said internal volume therethrough at a substantially normal angle of incidence to said surface within said internal volume, transmit through, (or reflect from), said sample caused to be present on said surface, and enter a detector. Typically such a third beam will not be subject to having a polarization state imposed thereupon and is utilized to determine intensity attenuation resulting from interaction, (transmission or reflection via beam splitter), with said sample.

Note that the terminology "effective" input and output windows is present to indicate that said windows can be locations on such as a prism shaped, semi-spherical shaped or half-cylinder shaped element, although a typical cell has physically separate input and output windows, and possibly a third window mounted therewithin.

A method of investigating fluid sample with at least two beams of electromagnetic radiation comprises the steps of:
  a. providing a system as described above;
  b. entering fluid sample into said cell internal volume so that it contacts said surface therewithin;
  c. causing a first beam of electromagnetic radiation to, at an oblique angle, approach said sample directly, (not through said stage); and
  d. causing a second beam of electromagnetic radiation to approach, at an oblique angle, said sample through said "stage" upon which it is supported.

Reflected components of each of the at least two electromagnetic beams are detected by one or more detector(s) and analyzed. (Single or multiple detector systems can be utilized). Particularly, but not exclusively, where a single detector system is used fiber optics can be used to guide electromagnetic radiation into different detector elements thereof.

It should also be appreciated that data is obtained from both "sides" of a sample present on said "stage" surface inside said cell internal volume. Use of the effective two data sets acquired as described in a simultaneous regression allows better determination of sample properties, such as uncorrelated thickness and refractive Index.

Another disclosed invention method of simultaneously investigating sample with at least two beams of electromagnetic radiation comprises the steps of:
  a. providing a system for enabling substantially simultaneous investigation of a fluid sample with at least two electromagnetic radiation beams, said system comprising a sample stage which has first and effective second surface sides;

such that in use one electromagnetic radiation beam is entered from the first surface side of said sample stage, and a second electromagnetic radiation beam is entered from the effective second surface side of said sample stage, each at an oblique angle thereto;
  b. providing a sample on said first surface of said sample stage;
  c. causing a first beam of electromagnetic radiation to approach said sample on said first surface from the first surface side of said sample stage; and
  d. substantially simultaneously with step c. causing a second beam of electromagnetic radiation to approach said sample on said first surface of the sample stage from the second effective surface side of said sample stage.

It is noted that the terminology "substantially simultaneously" is to be interpreted to include per se. simultaneous and at times separated by short delays, (eg. milli-seconds to seconds or longer).

It is also noted that the terminology "effective" second surface is used to indicate that said "effective" second surface need not be parallel to the first surface upon which is caused to be present sample. In particular an "effective" second surface can be a perimeter surface of a prism, semi-spherical or half-cylinder shaped beam entry element which is affixed to a cell, said beam entry element forming what might be termed a base to said cell.

Further, it should be appreciated that two electromagnetic beams can be of similar or different polarization states, wavelength content, can be applied at the same or different angles-of-incidence to a sample on the internal surface of the cell, and can be substantially simultaneously applied by elements of one, or more than one, ellipsometer system(s). For instance, a source of electromagnetic radiation can be configured to provide two beams, one beam being applied from the one side, and one from the other side of a sample stage. The two beams can be, for instance, guided via optical fibers from one or more than one sources. And, reflected beams can be caused to enter different detectors or the same detector, (eg. as directed by optical fibers).

A preferred embodiment provides that an electromagnetic beam directed toward one side of a sample stage surface be comprised of wavelength content which differs from that of a second beam of electromagnetic radiation directed to enter from the other of said sample stage surface. Another preferred embodiment provides that the two electromagnetic beams have similar, or different, wavelength contents but are directed toward the sample stage surface at different obliquie angles-of-incidence, (one from above and one from below the sample stage as the sytem is viewed in elevation). Another preferred embodiment provides that the two electromagnetic beams have similar, or different polarization states imposed thereupon.

It is specifically noted that the first and/or second electromagnetic beams mentioned above can be provided by a selection from the group consisting of:
  ellipsometer;
  polarimeter;

which monitor changes in both the ratio of magnitudes of orthogonal components of an electromagnetic beam and the phase angle therebetween, as a result of interaction with a sample; or by a selection from the group consisting of:
  reflectometer; and
  spectrophotometer;

which monitor change in intensity before and after interaction with a sample.

It is emphasized that the foregoing disclosed application of ellipsometric beams to, at oblique angles of incidence, investigate a sample from two sides thereof. It is again noted that a third electromagnetic beam, (eg. an unpolarized intensity beam), can be applied substantially normal to the effective surface upon which is present a fluid sample to enable acquiring beam attenuation transmission data, and said data can also be used in sample analysis.

U.S. Pat. No. 5,872,630 methodology for calibration of an ellipsometer, and U.S. Pat. No. 6,034,777 Patent methodology for breaking correlation between the effects of the input and output windows and a sample being investigated, which methodology was recited in the Background Section, can of course be added to the preceding recitations to provide more complete methodology.

The invention will be better understood by reference to the Detailed Description Section of this Specification, in conjunction with the Drawings.

SUMMARY OF THE INVENTION

It is therefore an objective and/or purpose of the invention to teach a system for applying at least two electromagnetic beams to investigate a sample.

It is another objective and/or purpose of the invention to teach a system including a fluid sample containing cell for applying at least two electromagnetic beams to investigate a fluid sample.

It is another objective and/or purpose of the invention to teach a system for applying at least two electromagnetic beams to investigate a fluid sample, which system comprises a cell that comprises effective electromagnetic beam input and output windows, means for entering a fluid sample thereinto, which system further comprises a beam entry element in functional combination with the second surface of said sample stage element.

It is another objective and/or purpose of the invention to teach a system for applying at least two electromagnetic beams to investigate a fluid sample, which system comprises a cell which comprises effective electromagnetic beam input and output windows, means for entering a fluid sample thereinto such that it comes into contact with an adjacent first surface of a sample stage element which has first and second, (preferably, but not necessarily, substantially parallel to the first), surfaces, and which system further comprises a beam entry element adjacent to the second surface of said sample stage element.

It is another objective and/or purpose of the invention to teach a method for applying at least two electromagnetic beams substantially simultaneously to a sample.

It is another objective and/or purpose of the invention to teach a method for applying at least two electromagnetic beams substantially simultaneously to sample, using the same, or different, ellipsometer, polarimeter, reflectometer or spectrophotometer system(s).

It is yet another objective and/or purpose of the invention to describe application of correction methodology to account for the effect of the birefringence of windows.

It is still yet another objective and/or purpose of the invention to describe simultaneous use of data obtained from both sides of a sample in arriving at values for its characterizing parameters.

Other objectives and/or purposes will become apparent by a reading of the Specification and claims.

BRIEF DESCRIPTION OF THE DRAWINGS

FIG. 5d shows that the (CELL) can have a specific Transmission Window (TW) available to allow a Transmission Intensity beam (EMT) to pass directly through at substantially normal incidence.

DETAILED DESCRIPTION

Figure 8:
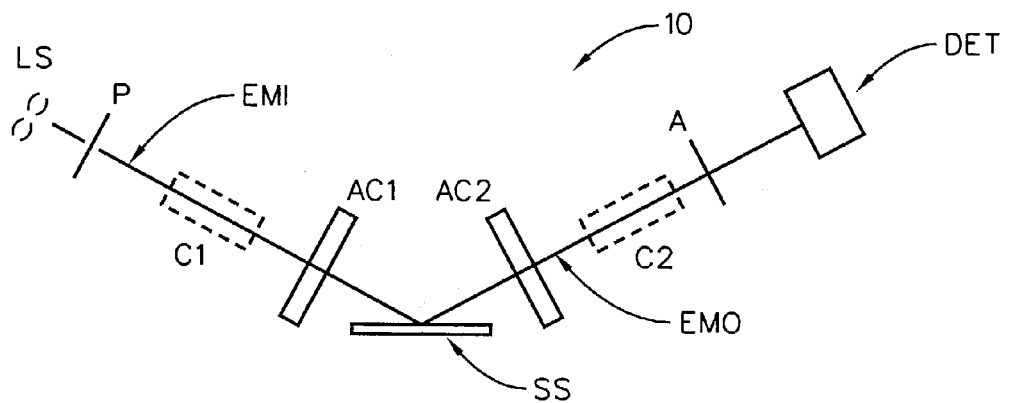
FIG. 8 shows a general elemental configuration of an ellipsometer system which can be applied to investigate a biologic sample.

To begin, for general insight it should be appreciated that FIG. 8 demonstrates an ellipsometer system which can be applied to investigate a sample system (SS). Shown are, sequentially:

a. a Source of a beam electromagnetic radiation (LS);
b. a Polarizer element (P);

c. optionally a compensator element (C1);
d. (additional element(s)) (AC1);
e. a sample system (SS);
f. (additional element(s)) (AC2);
g. optionally a compensator element (C2);
h. an Analyzer element (A); and
i. a Detector System (DET).

It is noted that the elements identified as (LS), (P) and (C1) can be considered to form, as a group, a Polarization State Generator (PSG), and the components (C2), (A) and (DET) can be considered, as a group, to form a Polarization State Detector (PSD). It is to be understood that the d. and f. "additional elements", (AC1) and (AC2), can be considered as being, for the purposes of the disclosed invention Disclosure, input and output cell (CELL) input (WI) and output (WO) window means. Note the locations of electromagnetic beams (EMI) and (EMO).

Figure 1:
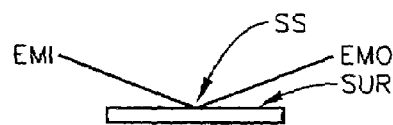
FIG. 1, there is shown a conventional arrangement wherein an incident electromagnetic beam (EMI) entered from atop, (oriented as shown), reflects from a sample (SS) as output electromagnetic beam (EMO).
Figure 2:
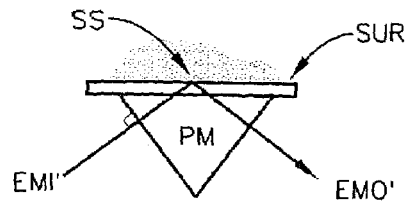
FIG. 2 shows access to a sample (SS) from below, (oriented as shown), including a prism shaped beam entry element (PM) with sides sloped such that entering (EMI) and exiting (EMO') electromagnetic beams approach perpendicularly to said sides.

Turning now to FIG. 1, there is demonstrated a conventional reflectometer, polarimeter ellipsometer or the like system incident electromagnetic beam (EMI) entered from atop, (oriented as shown), which electromagnetic beam reflects from a sample (SS) positioned on a surface (SUR) and becomes output electromagnetic beam (EMO). FIG. 2 shows that it is also known to access a sample (SS) from below, (oriented as shown) a surface (SUR) of a sample stage element (STG). Note that FIG. 2 provides a prism shaped beam entry element (PM) with sides sloped such that entering (EMI') and exiting (EMO') electromagnetic beams approach perpendicularly to the sides thereof. Note the location of sample stage element (STG) surface (SUR) in FIGS. 1 and 2, upon which the sample (SS) is present.

Figure 3:
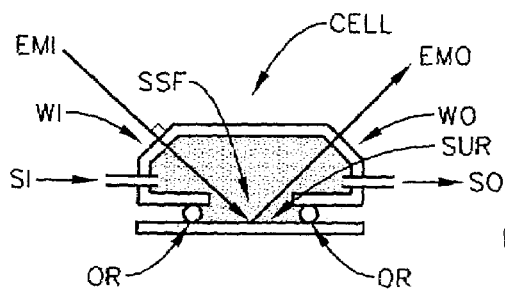
FIG. 3 demonstrates a cell (CELL) into which fluid sample (SSF) can be entered, said cell (CELL) having input (WI) and output (WO) windows through which electromagnetism can be caused to enter as electromagnetic beam (EMI) and, after reflection from a surface upon which the fluid sample (SSF) is caused to contact, exit as electromagnetic beam (EMO).

FIG. 3 demonstrates that disclosed invention practice preferably involves use of a cell (CELL) into which fluid sample (SSF) can be entered, said cell (CELL) having input (WI) and output (WO) windows through which electromagnetism can be caused to enter as electromagnetic beam (EMI), which after reflecting from a fluid sample (SSF) present on sample stage element (STG) surface (SUR), exits as electromagnetic beam (EMO). Said cell (CELL) typically has at least one opening through the lower, (oriented as shown), wall thereof through which fluid sample (SSF) exits onto said sample stage element (STG) surface (SUR). Said cell (CELL), in use, is caused to sit atop said sample stage (STG) surface (SUR) with such as an "O" (OR) rings mediating said contact therewith and forming a space therewithin atop said surface (SUR) wherein fluid sample (SSF) is contained. Also shown is a means for entering and exiting fluid sample (SS) Into and out of the cell (CELL). It will be appreciated that the FIG. 3 sample stage element (STG) surface (SUR) is the same as the first surface of the sample stage element (STG) described in the Disclosure of the Invention Section of this Specification.

It should be appreciated that if, for instance, the fluid sample (SSF) which is entered into the cell (CELL) is opaque to a wavelength of electromagnetic radiation, then a beam of said electromagnetic radiation entered (EMI) to the cell (CELL) through the input window (WI) will not reach the location at which it can reflect from the fluid sample present on said surface (SUR), and then exit through the exit window (WO). In such a case it is known to apply the beam of electromagnetic radiation (EMI') from below the sample stage element (STG) surface (SUR) upon which the sample (SS) is present, assuming said sample stage element (STG) is of a material which is transparent to said wavelength. As mentioned above, FIG. 2 shows such an arrangement. Note that FIG. 2 shows that a Prism (PM) beam entry element (BEE) is present beneath the sample stage element (STG) to facilitate an angle of incidence entry and exit of the electromagnetic radiation. A preferred arrangement has a beam of electromagnetic radiation enter and exit a side of a Prism (PM) along a locus which is perpendicular to the relevant Prism (PM) surface. Different Prisms allow use of different angles of incidence.

Figure 4:
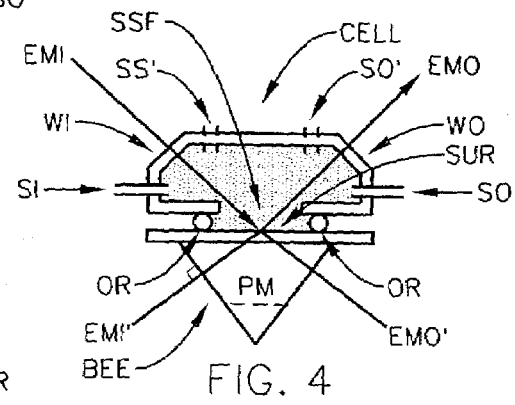
FIG. 4 shows a disclosed invention configuration, which allows investigation of a fluid sample (SSF) present on a surface, with two beams, either alternatingly, simultaneously or at times separated by only a short time delay.
Figure 5A:
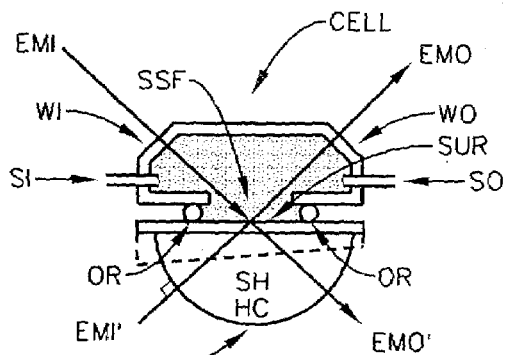
FIG. 5a shows, as distinguished from the FIG. 4 use of a Prism (PR), a Semi-Spherical (SH) or Half-Cylinder (HC) shaped beam entry element present beneath the surface, so as to provide for variable angles of incidence entry (EMI') and exit (EMO') of the electromagnetic radiation.

FIG. 4 shows a disclosed invention system configuration which allows investigation of a fluid sample (SSF) present on a first surface (SUR) of a sample stage element (STG), with two electromagnetic beams, either alternatingly, simultaneously or at times separated by only a short time delay. One electromagnetic beam is entered as electromagnetic beam (EMI) through an input window (WI) of a cell (CELL) which is situated atop said first sample stage element (STG) surface, and the other electromagnetic beam is entered from below said first sample stage element (STG) surface through a Prism (PM) or, as shown in FIG. 5a, preferably through a Semi-Spherical (SH) or Half-Cylinder (HC), (said semisphere being shown in elevation and said half-cylinder (HC) being interpreted as shown in cross-section), shaped beam entry element (BEE) which is present beneath the second surface of the sample stage element (STG), so as to provide for variable angles of incidence entry (EMI') and exit (EMO') of the electromagnetic radiation while maintaining the surface perpendicularity to the beam entry element surface. That is, in FIG. 5a, any angle of incidence, (in the plane of the paper for a half cylinder (HC) cross-section shaped element), of (EMI') and (EMO'), can be utilized while maintaining a entry and exit loci perpendicular to the (SH) (HC) element surface. As in FIG. 3, the cell (CELL) has means for entering (SI) and exiting (SO) fluid sample (SSF) into and out of the cell (CELL), and it is to be understood that said entering (SI) and exiting (SO) can be located other than where shown if function is maintained, (eg. one or both entering (SI) and exiting (SO) means can be located in the top of the cell (CELL), as demonstrated by (SI') and (SO'). Note that for completeness, there dashed indication that the first and second surfaces of the sample stage element (STG) need not be parallel to one another, though preferred practice is that they be so parallel.

It is also to be understood that the "O" ring (OR) in FIG. 4 can be an integrated connection element between the cell (CELL) and the first surface (SUR) of the sample stage element such that said cell (CELL) and the sample stage element (STG) are of a one-piece construction, and/or the sample stage element (STG) and beam entry element (eg. (PM) in FIG. 4 and (SH) or (SC) in FIG. 5a), can be of an integrated single piece structure. Two piece and single piece systems are then also within the scope of the disclosed invention.

The dashed line in the FIG. 4 prism (PR) is to indicate that materials therebelow can be removed without adversely affecting the function of said prism (PR).

Figure 5B:
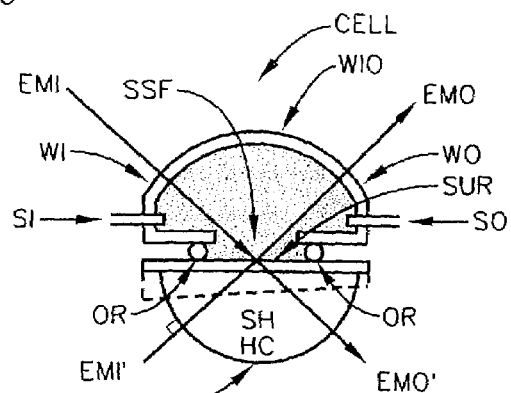
FIG. 5b shows FIG. 5a with a modification to provide a Semi-Spherical (SH) or Half-Cylinder (HC) element (WIO) in place of the input (WI) and output (WO) windows therein.

FIG. 5b shows FIG. 5a with a modification to provide a Semi-Spherical (SH) or Half-Cylinder (HC) element (WIO) in place of the input (WI) and output (WO) windows therein.

Figure 5C:
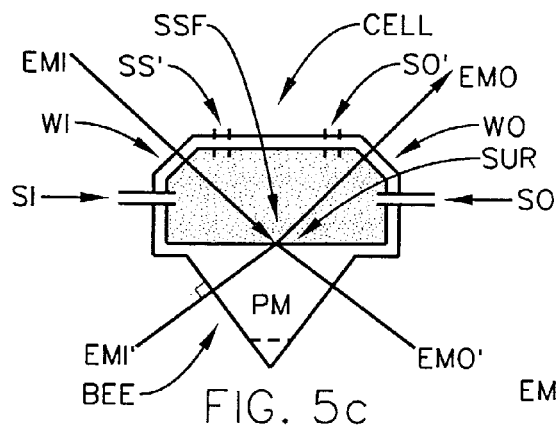
FIGS. 5c, 5d and 5e show "integrated" systems in which the Stage is not specifically identifiable as a separate element but is present only functionally in that it provides a first surface (SUR) and an effective second surface (BEE) which, as shown, is other than substantially parallel to the first surface (SUR). The identifiers are the same as in FIGS. 5a and 5b.
Figure 5D:
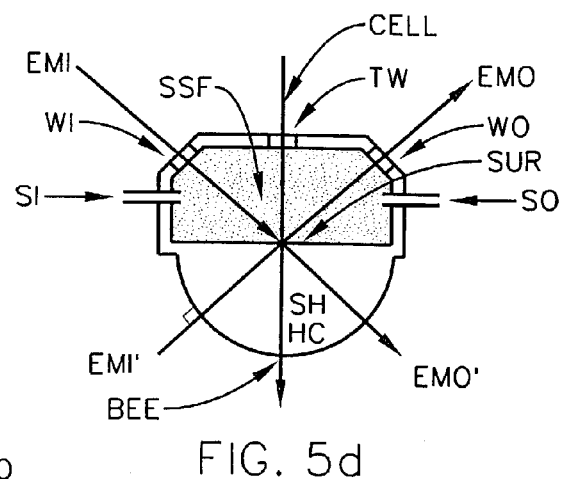
Figure 5F:
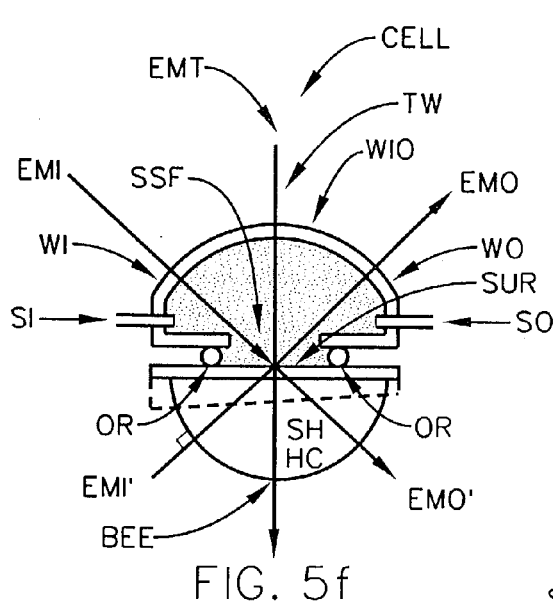
FIG. 5f shows FIG. 5b with a normal beam of electromagentic radiation also present.
Figure 5E:
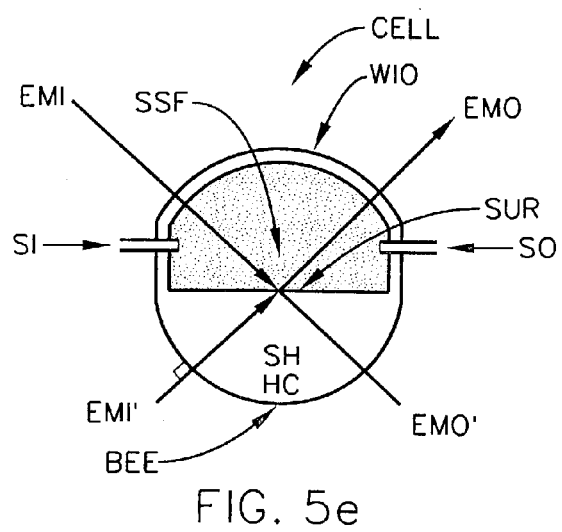

FIGS. 5c, 5d and 5e show "integrated" systems in which a Stage, (ie. (STG) as shown in FIGS. 5a and 5b), is not specifically identifiable as a separate element but is present functionally in that it again provides a first surface (SUR), and an "effective" second surface, (ie. the perimeter of the beam entry element (BEE), which, as shown, is generally other than substantially parallel to the first surface (SUR)). It is to be appreciated that it is the function performed which is the focus of the disclosed invention and that the various examples are demonstrative rather than limiting. FIG. 5d shows that the (CELL) can have a specific Transmission Window (TW) available to allow a Transmission Intensity beam (EMT) to pass directly through at a substantially normal incidence to the sample on the first stage surface. This allows analysis of a sample using oblique angles of incidence of electromagnetic beams applied to two sides thereof, in combination with use of a Transmission Intensity Beam (EMT) absorbence. It is noted that simultaneous use of multiple sets of data enables uncorrelated determination of thickness and refractive index of a sample. This is similar to the result obtained when data is obtained from two similar composition substrates and a simultaneous regression of mathematical models for each, onto its respective data set, is performed. Said procedure enables separately determining the thickness of each substrate, and the refractive index therefore, where if only one mathematical model and data set is present, only the product of the thickness and refractive index can be determined. FIG. 5f shows FIG. 5b with a normal beam of electromagnetic radiation also present.

Figure 6:
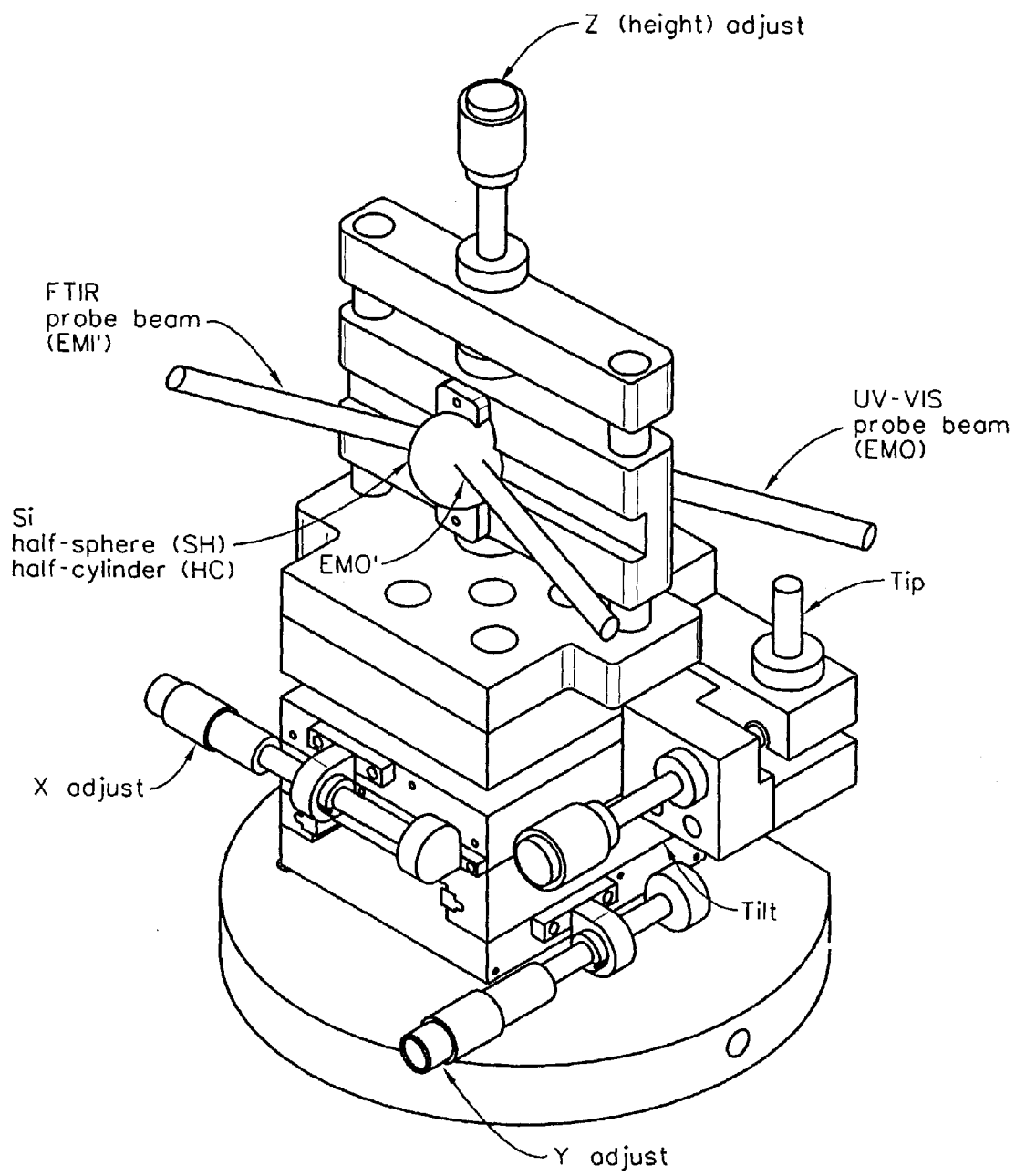
FIG. 6 demonstrate a physical apparatus which can be applied to contain the FIGS. 4 and 5 system for enabling alternating, simultaneous, or at times separated by only a short delay, Investigation of fluid sample (SSF) with two (IR and UV wavelength content) electromagnetic radiation beams.
Figure 7:
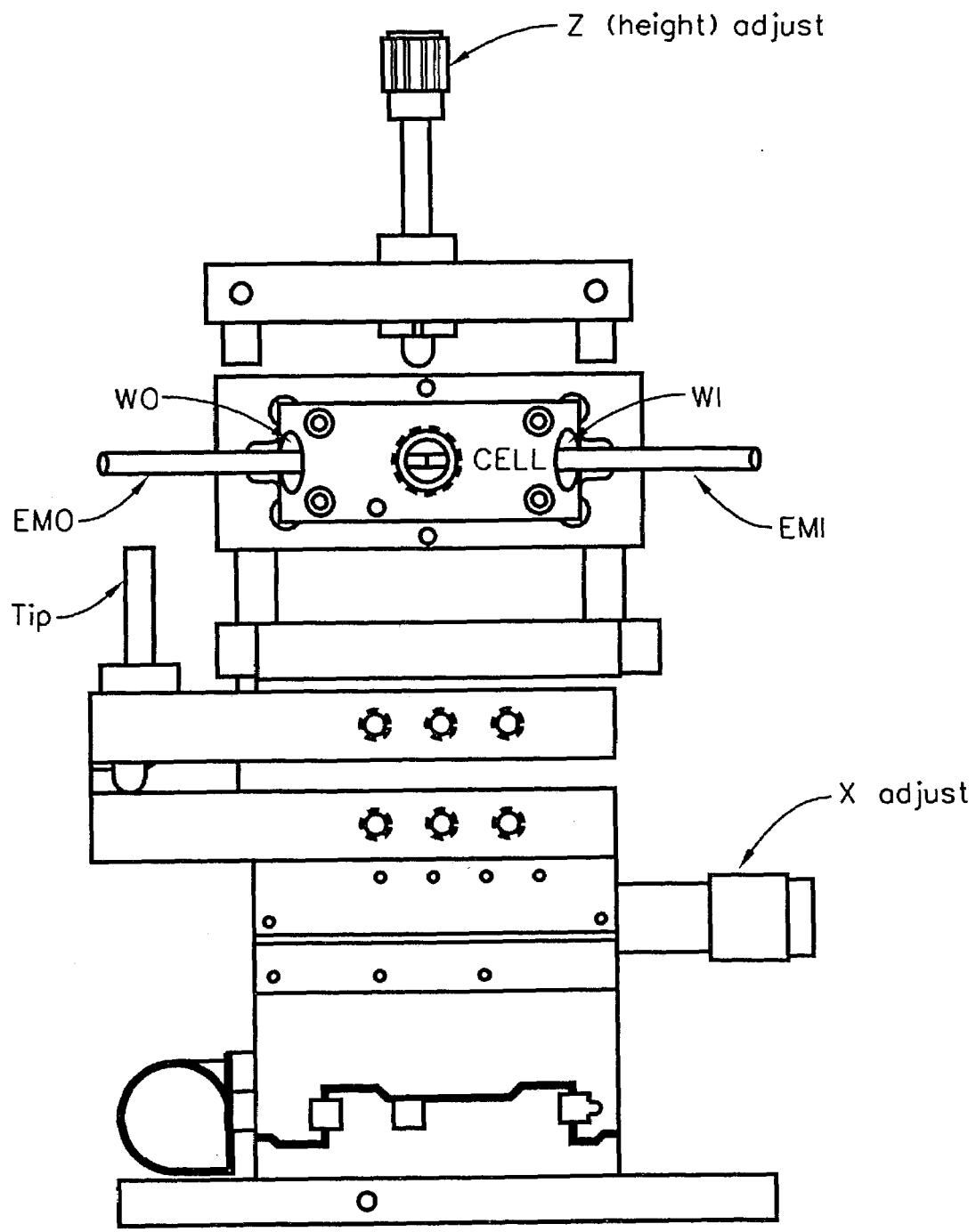
FIG. 7 shows the system of FIG. 6, looking from the back side thereof.

FIG. 6 demonstrates a physical apparatus which contains the FIGS. 4 and 5a system for enabling alternatingly, simultaneous, or at times separated by only a short delay, investigation of fluid sample (SSF) with two, (eg. IR and UV wavelength content), electromagnetic radiation beams. FIG. 6 shows the FIGS. 4 and 5a system oriented with the bottom in said FIGS. 4 and 5a oriented to the left. Note that one electromagnetic radiation beam containing (UV) is entered through an input window oriented at the back of FIG. 6, and the other electromagnetic radiation beam containing (IR) is shown being entered from the left in FIG. 6. Also shown are various means for controlling height (Z), lateral (X), depth (Y), and Tilt and Tip. FIG. 7 shows the system of FIG. 6, looking from the back side thereof.

Figure 9:
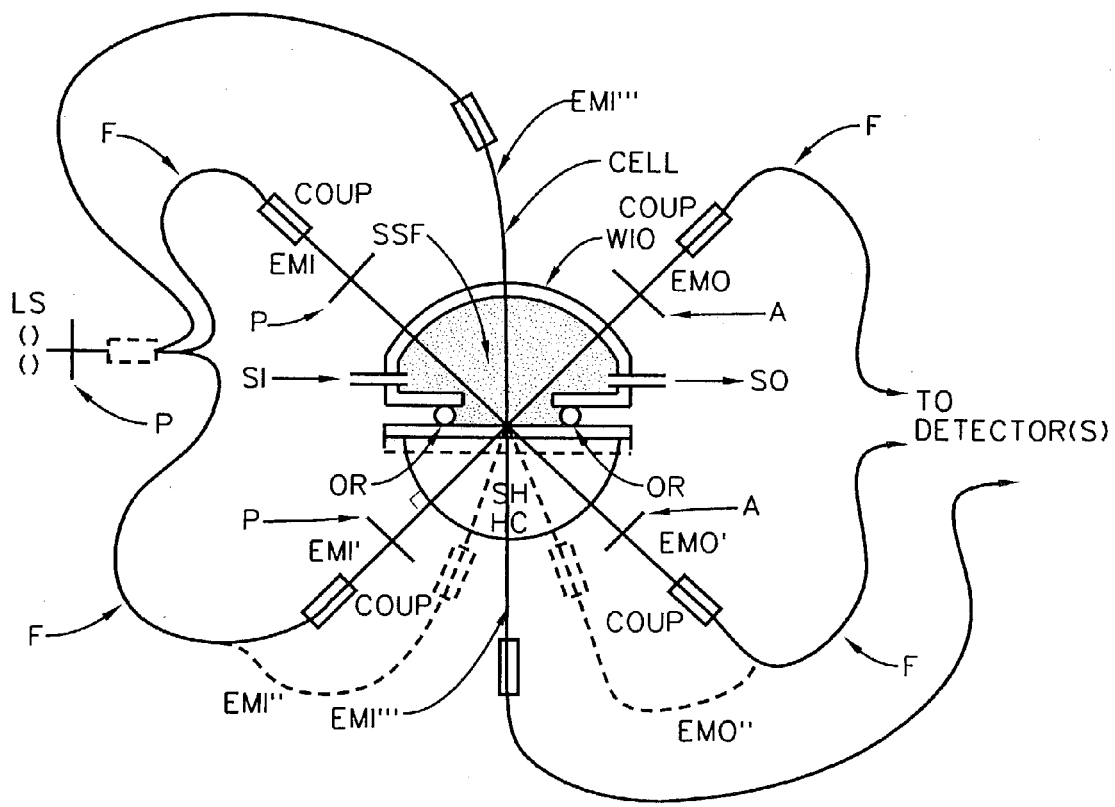
FIG. 9 shows a Cell comprising a surface (SUR) of a sample stage element (STG) which is provided electromagnetic radiation EMI and EMI' from a single source, and further indicates reflected beams EMO and EMO' can be directed to one or more Detector(s).

FIG. 9 shows a Cell as in FIG. 5b, comprising a surface (SUR) of a sample stage element (STG) which is provided electromagnetic radiation EMI and EMI' or EMI" from a single source via divider means, (or separate sources could be used), and further indicates reflected beams EMO and EMO' are directed to one or more Detector(s). It is to be understood that the electromagnetic beams EMI and EMI' can comprise the same or different wavelength content. For instance, the same wavelength content can be present in EMI and EMI" and different angles-of-incidence from above and below utilized, as indicated by EMI and dashed line EMI". Different wavelength content can also be present in EMI and EMI". Where different wavelength content is present, the beams EMI and EMI' can be applied at the same angle-of-incidence, however, in this case the same wavelength content could be present and the purpose behind the configuration being solely to gain data pertaining to top and bottom aspects of a sample atop the surface of the sample stage element (STG). Normal angle of incidence electromagnetic beam EMI''' is indicated as present as well, but no Polarizer or Analyzer is typically present in the EMI''' beam locus. That is EMI''' is a Transmission Intensity beam used to monitor sample absorbance. Note that optical fibers (F) and Couplers COUP) can be utilized to guide incident and reflected electromagnetic beams. Also note that Analyzer(s) (A), Polarizers (P) and optional Compensator(s) (C1) (C2) along with the Detectors(s) indicated as shown in FIG. 8, are assumed present in FIG. 9 as functionally required. Note, where different wavelengths are to be provided in the multiple electromagnetic beams, utilizing a single source of electromagnetic radiation in combination with Couplers which including functional filtering means, is a possibility. Further it should be appreciated that a source of electromagnetic radiation can be comprised of multiple sources and a beam combiner, as taught in U.S. Pat. No. 6,268,917 to Johs.

What it is believed has not previously been known is a system for, and method of applying two electromagnetic beams, one from one side, and a second from a second side of an element which presents with two, preferably substantially parallel, surfaces, said electromagnetic beams being applied alternatingly, simultaneously or with only a short time delay therebetween. Said electromagnetic beams are typically chosen to be of different wavelengths, with the benefit being that measurements at said different wavelengths can be conducted without the need to change electromagnetic radiation source and detector arrangements, and that characteristics of a sample can be determined at two wavelengths without the sample having had time to undergo significant change between said measurements.

It is to be understood that there term "fluid" is to be interpreted to Include both liquid and solid sample which can be caused to flow into cell (CELL), and the terminology "fluid sample" further includes a film present on the first sample stage element surface, whether placed there as a film or formed there by application of a fluid sample entered into the cell (CELL) through said means for entering fluid sample into.

It is also the be understood that the terminology "Input Window" and "Output Window" as shown in FIGS. 4 and 5a as (WI) and (WO), for instance, are to be interpreted to include a FIG. 5b system means (WIO) where no defined cell (CELL) "Windows" per se. are delineated, but rather a "continuous" window (WIO) is present via which electromagnetic radiation is entered toward and exited from said first sample stage element surface. Any such window means are termed "effective" first and/or effective second windows in the claims. The terminology "effective" input and/or "effective" output windows in the claims is also to be read to cover the case wherein a beam entry element such as (PM) in FIG. 4 or (SH)(HC) in FIG. 5a is utilized to enter and exit electromagnetic radiation toward and from the second sample stage element surface.

It is to be further noted that a beam of electromagnetic radiation can be unpolarized, polarized to comprise two ("p" and "s") orthogonal components, or to comprise one ("p" and "s") orthogonal component, including the case wherein a single "p" or "s" component is obliquely applied to a sample system.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the claims.

We claim:

1. A system for enabling substantially simultaneous investigation of a fluid sample with at least two electromagnetic radiation beams, said system comprising a cell, said cell comprising:

effective input and output windows;

input and output means for entering and exiting fluid sample;

an internal volume presenting with a surface therewithin; said system further comprising, in functional combination with said cell, a beam entry element being located, as said system is viewed in upright side elevation, below said surface;

such that in use fluid sample is entered to the internal volume of said cell through said input means for entering fluid sample, such that it contacts said surface within said internal volume, and such that one electromagnetic radiation beam is entered through said effective input window of said cell, and a second electromagnetic radiation beam is entered through said beam entry element, to the end that both said first and second electromagnetic beams interact with said fluid sample present on said surface in said internal volume of said cell, each being impinged thereupon obliquely with respect to said surface, so that they then reflect from said sample, exit and enter detector means.

2. A system as in claim 1, in which said cell comprises a third effective window and wherein a third electromagnetic beam is caused to enter said internal volume therethrough at a substantially normal angle of incidence to said surface within said internal volume, transmit through said fluid sample caused to be present on said surface, and enter a detector.

3. A system as in claim 1, in which the beam entry element through which said second electromagnetic radiation beam is entered is of a shape selected from the group consisting of:
   prism;
   semi-spherical; and
   half-cylinder.

4. A system as in claim 1, in which the effective input and output windows are characterized by being portions of an element which is of a shape selected from the group consisting of:
   prism;
   semi-spherical; and
   half-cylinder.

5. A system as in claim 1, in which the effective input and output and third effective windows are separate elements.

6. A system as in claim 1, in which the cell and beam entry element are integrated to form a continuous construction.

7. A system as in claim 2, in which the first, second and third electromagnetic beams are characterized by selections from the group consisting of:
   each being of substantially the same wavelength content;
   at least two thereof being of different wavelength content;
   at least one being set to a polarization state;
   at least one being unpolarized;
and the first and second electromagnetic beams are each further characterized by:
   being applied to a sample at the same magnitude oblique angles-of-incidence;
   being applied to a sample at different magnitude oblique angles-of-incidence;
with to respect to said surface.

8. A system as in claim 1, in which the first and/or second electromagnetic beams is/are provided by selection(s) from the group consisting of:
   ellipsometer;
   polarimeter;
   reflectometer; and
   spectrophotometer;
said selected ellipsometer, polarimeter, reflectometer or spectrophotometer being comprised of at least one source of electromagnetic radiation, and at least one detector thereof, which source(s) and detector(s) are oriented so that electromagnetic radiation produced by the source(s) is caused to interact with the fluid sample caused to be present on said surface within the internal volume of said cell, and then enter said detector(s); said selected ellipsometer, polarimeter, reflectometer or spectrophotometer further comprising in the path of at least one electromagnetic beam a polarizer means between said source(s) and said fluid sample, and analyzer means between said fluid sample and said detector(s).

9. A system as in claim 1, in which the first and second electromagnetic radiation beams are provided by a single source of electromagnetic radiation.

10. A system for enabling substantially simultaneous investigation of a fluid sample with at least two electromagnetic radiation beams, comprising a sample stage element having a first sample stage element surface, and a second sample stage element surface, said system further comprising a cell in functional combination with said first sample stage element surface, said cell comprising:
   effective input and output windows;
   input and output means for entering and exiting fluid sample;
   an internal volume which has an opening adjacent to said first sample stage element surface such that fluid sample entered into said cell via said input means there of can access said first sample stage element surface;
said system further comprising a beam entry element in functional combination with and adjacent to said second sample stage element surface;
such that in use fluid sample is entered to the internal volume of said cell through said input means for entering fluid sample, and a first electromagnetic radiation beam is entered through said effective input window of said cell which is adjacent to said first sample stage element surface, and a second electromagnetic radiation beam is entered through said beam entry element adjacent to said second sample stage element surface, to the end that both said first and second electromagnetic beams interact with said fluid sample present in said internal volume of said cell, on said first sample stage element surface, then exit and enter detector means.

11. A system as in claim 10, in which said cell comprises a third window and wherein a third electromagnetic beam is caused to enter said internal volume therethrough at a substantially normal angle of incidence to said first sample stage element surface within said internal volume, transmit through said fluid sample caused to be present on said first sample stage element surface, and enter a detector.

12. A system as in claim 10, in which the beam entry element through which said second electromagnetic radiation beam is entered is of a shape selected from the group consisting of:
   prism;
   semi-spherical; and
   half-cylinder.

13. A system as in claim 10, in which the cell is separated from said first sample stage element surface by "O" ring means, such that fluid sample entered into said cell becomes present within said "O" ring means on said first sample stage element surface.

14. A system as in claim 10, in which the cell and first sample stage element surface are integrated to form a continuous construction.

15. A system as in claim 10, in which the second sample stage element surface and the beam entry element are integrated to form a continuous construction.

16. A system as in claim 10, in which the cell and first sample stage element surface are integrated to form a continuous construction, and in which the second sample stage element surface and the beam entry element are integrated to form a continuous construction.

17. A system as in claim 11, in which the first and second electromagnetic beams are characterized by selections from the group consisting of:
  each being of substantially the same wavelength content;
  at least two thereof being of different wavelength content;
  at least one being set to a polarization state;
  at least one being unpolarized;
and the first and second electromagnetic beams are each further characterized by:
  being applied to a sample at the same magnitude oblique angles-of-incidence;
  being applied to a sample at different magnitude oblique angles-of-incidence;
with to respect to said surface.

18. A system as in claim 10, in which the first sample stage element surface and second sample stage element surface are related to one another by a selection from the group consisting of:
  being substantially parallel to one another; and
  being other than substantially parallel to one another.

19. A system as in claim 10, in which the first and/or second electromagnetic beams is/are provided by selection(s) from the group consisting of:
  ellipsometer;
  polarimeter;
  reflectometer; and
  spectrophotometer;
said selected ellipsometer, polarimeter, reflectometer or spectrophotometer being comprised of at least one source of electromagnetic radiation, and at least one detector thereof which source(s) and detector(s) are oriented so that electromagnetic radiation produced by the source(s) is caused to interact with the fluid sample caused to be present in said cell, and then enter said detector(s); said selected ellipsometer or polarimeter further comprising a polarizer and/or compensator means between said source(s) and said fluid sample, and analyzer and/or compensator means between said fluid sample and said detector(s).

20. A system as in claim 10, in which the first and second electromagnetic beams are provided by a single source of electromagnetic radiation.

21. A method of investigating fluid sample with multiple beams of electromagnetic radiation comprising the steps of:
  a) providing a system for enabling substantially simultaneous investigation of a fluid sample with at least two electromagnetic radiation beams, said system comprising a cell, said cell comprising:
    effective input and output windows;
    input and output means for entering and exiting fluid sample;
    an internal volume presenting with a surface therewithin;
  said system further comprising a beam entry element in functional combination with said cell, and being located, as viewed in upright side elevation, below said surface within said cell;
  such that in use fluid sample is entered to the internal volume of said cell through said input means for entering fluid sample, such that it contacts said surface within said internal volume, and such that one electromagnetic radiation beam is entered through said effective input window of said cell, and a second electromagnetic radiation beam is entered through said beam entry element, to the end that both said first and second electromagnetic beams interact with said fluid sample present on said surface in said internal volume of said cell, each at an oblique angle to said surface, then reflect from said sample, exit and enter detector means;
  b) entering fluid sample into the internal volume of said cell and become present on said surface in said internal volume of said cell;
  c) causing a first electromagnetic radiation beam to enter said effective input window; and
  d) causing a second electromagnetic radiation beam to enter said beam entry element;
to the end that both said first and second electromagnetic beams approach said sample on said surface in said internal volume of said cell at oblique angles thereto and interact with said fluid sample present thereupon, and then exit and enter detector means.

22. A method of investigating fluid sample with multiple beams of electromagnetic radiation as in claim 21, which further comprises, in the step of providing a system for enabling substantially simultaneous investigation of a fluid sample with at least two electromagnetic radiation beams, providing an additional effective input window, said additional window being positioned to allow entry of an electromagnetic beam along an effective normal to said sample on said surface in said internal volume of said cell, such that it transmits therethrough and is then caused to enter a detector means.

23. A method of simultaneously investigating sample with at least two beams of electromagnetic radiation comprising the steps of:
  a) providing a system for enabling substantially simultaneous investigation of a fluid sample with at least two electromagnetic radiation beams, comprising a sample stage element which has a first surface, and an effective second surface;
such that in use one electromagnetic radiation beam is entered from the first surface side of said sample stage element, and a second electromagnetic radiation beam is entered from the effective second surface side of said sample stage element;
  b) providing a fluid sample on said first surface of said sample stage element;
  c) causing a electromagnetic radiation beam to approach said fluid sample on said first surface of said sample stage element from the first surface side of said sample stage element; and
  d) substantially simultaneously with step c causing a second electromagnetic radiation beam to approach said fluid sample on said first surface of said sample stage from the effective second sample stage surface side;
to the end that both said first and second electromagnetic beams interact with said fluid sample and enter detector means.

24. A method of simultaneously investigating sample with at least two beams of electromagnetic radiation comprising the steps of:
  a) providing a system for enabling substantially simultaneous investigation of a fluid sample with two electromagnetic radiation beams comprising a cell, said cell comprising:
    spatially separated effective input and output windows;
    input and output means for entering and exiting fluid sample;
    an internal volume which is partially comprised of a first surface of a sample stage;
  said system further comprising a beam entry element in functional combination with said cell, said beam entry element comprising an effective second surface of said sample stage;

such that in use fluid sample is entered to said internal volume of said cell through said input means for entering fluid sample, such that it becomes located on said first surface of said sample stage, and such that one electromagnetic radiation beam is entered through said effective input window of said cell, and a second electromagnetic radiation beam is entered through said effective second surface of said sample stage, in said beam entry element;

b) causing a sample to be present on said first surface of said sample stage by entering fluid sample to the internal volume of said cell;

c) causing a first electromagnetic radiation beam to approach said sample on said first surface of said sample stage from the first surface side of said sample stage; and d) causing a second electromagnetic radiation beam to approach said sample on said first surface of said sample stage from the effective second sample stage surface side;

to the end that both said first and second electromagnetic beams interact with said fluid sample present in said internal volume of said cell, and then exit and enter detector means.

25. A method of simultaneously investigating sample with at least two beams of electromagnetic radiation as in claim 24, said method further comprising accurately evaluating parameters in parameterized equations in a mathematical model of said system comprising said spatially separated effective input and output windows, said parameterized equations enabling, when parameters therein are properly evaluated, independent calculation of retardation entered by each of said effective input output windows between orthogonal components of a beam of electromagnetic radiation caused to pass through said effective input and output windows, at least one of said effective input and output windows being bi-refringent, which method of accurately evaluating parameters in parameterized equations in a mathematical model of said system comprising said spatially separated effective input and output windows, comprises, in a functional order, the steps of:

a1) providing said spatially separated effective input and output windows, at least one of which effective input and output windows demonstrates birefringence when a beam of electromagnetic radiation is caused to pass therethrough, and further providing said means for supporting a sample system positioned between said effective input and output windows;

b1) positioning an ellipsometer system source of electromagnetic radiation and an ellipsometer system detector system such that in use a beam of electromagnetic radiation provided by said source of electromagnetic radiation is caused to pass through said effective input window, interact with a sample, in a plane of incidence thereto, and exit through said effective output window and enter said detector system;

c1) providing a sample to said means for supporting a sample system, the composition of said sample system being sufficiently well known so that retardance entered thereby to a polarized beam of electromagnetic radiation of a given wavelength, which is caused to interact with said sample system in a plane of incidence thereto, can be accurately modeled mathematically by a parameterized equation which, when parameters therein are properly evaluated, allows calculation of retardance entered thereby between orthogonal components of a beam of electromagnetic radiation caused to interact therewith in a plane of incidence thereto;

d1) in conjunction with other steps, providing a mathematical model for said ellipsometer system and said effective input and output windows, which comprises separate parameterized equations for independently calculating retardance entered between orthogonal components of a beam of electromagnetic radiation caused to pass through each of said effective input and output windows; such that where parameters in said mathematical model are properly evaluated, retardance entered between orthogonal components of a beam of electromagnetic radiation which passes through each of said effective input and output window, and further interacts with said sample system in a plane of incidence thereto can be independently calculated from said parameterized equations;

e1) obtaining a spectroscopic set of ellipsometric data with said parameterizable sample system present on the means for supporting a sample system, utilizing a beam of electromagnetic radiation provided by said source of electromagnetic radiation, said beam of electromagnetic radiation being caused to pass through said effective input window, interact with said parameterizable sample system in a plane of incidence thereto, and exit through said effective output window;

f1) by utilizing said mathematical model provided in step d and said spectroscopic set of ellipsometric data obtained in step e, simultaneously evaluating parameters in said mathematical model parameterized equations for independently calculating retardance entered between orthogonal components in a beam of electromagnetic radiation caused to pass through said effective input window, interact with said sample in a plane of incidence thereto, and exit through said effective output window;

to the end that application of said parameterized equations for each of said effective input and output window and sample for which values of parameters therein have been determined in step f1, enables independent calculation of retardance entered between orthogonal components of a beam of electromagnetic radiation by each of said effective input and output windows, and said sample system, at given wavelengths in said spectroscopic set of ellipsometric data, said calculated retardance values for each of said effective input window, effective output window and sample system being essentially uncorrelated.

26. A method as in claim 24, in which step d1 involves provision of a mathematical model for said ellipsometer system and said effective input and output windows parameterizable sample, can involve, for each of said input and output windows, providing separate parameterized mathematical model equations for retardance entered to each of said two orthogonal components of a beam of electromagnetic radiation caused to pass through said effective input and output windows; at least one of said orthogonal components for each of said effective input and output electromagnetic beam intercepting angle-of-incidence changing systems being directed out of the plane of incidence of said electromagnetic beam onto said parameterizable sample system; such that calculation of retardation entered between orthogonal components of said beam of electromagnetic radiation, by said effective input window is provided by comparison of retardance entered to each of said orthogonal components for said effective input window, and such that calculation of retardation entered between orthogonal components of said beam of electromagnetic radiation, by said effective output window is provided by comparison of retardance entered to each of said orthogonal components for said effective output window.

27. A method as in claim 24, in which step f1 provides for simultaneous evaluation of parameters in said mathematical model parameterized equations for said parameterizable sample system, and for said effective input and output windows, is preferably achieved by a square error reducing mathematical curve fitting procedure.

28. A method as in claim 24, in which step b1, provides for positioning of an ellipsometer system source of electromagnetic radiation and an ellipsometer system detector system and typically includes positioning a polarizer between said source of electromagnetic radiation and said effective input window, and the positioning of an analyzer between said effective output window and said detector system, and the step e obtaining of a spectroscopic set of ellipsometric data typically involves obtaining data at a plurality of settings of at least one component selected from the group consisting of:
   said analyzer; and
   said polarizer.

29. A method as in claim 24, in which in the step of providing mathematical model parameterized equations for enabling independent calculation of retardance entered by said effective input and said effective output window and a sample system between orthogonal components of a beam of electromagnetic radiation, can involve use of parameterized equations having a form selected from the group consisting of:

$$ret(\lambda)=(K1/\lambda)+(K2/\lambda 2)+(K3/\lambda 4))$$

$$ret(\lambda)=(K1/\lambda)$$

$$ret(\lambda)=(K1/\lambda)*(1+(K2/\lambda 2))$$

$$ret(\lambda)=(K1/\lambda)*(1+(K2/\lambda 2)+(K3/\lambda 4)).$$

30. A system for enabling substantially simultaneous investigation of a fluid sample with two electromagnetic radiation beams, said system comprising a cell, said cell comprising:
   effective input and output windows;
   input and output means for entering and exiting fluid sample;
   an internal volume;
said system further comprising a beam entry element in functional combination with said cell, and being located, as viewed in upright side elevation, below said cell;
such that in use fluid sample is entered to the internal volume of said cell through said input means for entering fluid sample, and one electromagnetic radiation beam is entered through said effective input window of said cell, and a second electromagnetic radiation beam is entered through said beam entry element;
in which system the first and/or second electromagnetic radiation beams is/are provided by selection(s) from the group consisting of:
   ellipsometer;
   polarimeter;
   reflectometer; and
   spectrophotometer;
said selection(s) being comprised of at least one source of electromagnetic radiation, and at least one detector thereof, which source(s) and detector(s) are oriented so that electromagnetic radiation produced by the source(s) is caused to interact with the fluid sample which is present in said cell, and then enter said detector(s); said selected ellipsometer and/or polarimeter further comprising a polarizer means and/or compensator means between said source(s) and said fluid sample, and analyzer means and/or compensator means between said fluid sample and said detector(s).

31. A system as in claim 30, in which said cell comprises a third window and wherein a third beam is caused to enter said internal volume therethrough at a substantially normal angle of incidence, transmit through said sample caused to be present on said first sample stage element surface, and enter a detector.

32. A system as in claim 30, in which the beam entry element through which said second electromagnetic radiation beam is entered is of a shape selected from the group consisting of:
   prism;
   semi-spherical; and
   half-cylinder.

33. A system as in claim 30, in which the effective input and output windows are characterized by being portions of an element which is of a shape selected from the group consisting of:
   prism;
   semi-spherical; and
   half-cylinder.

34. A system as in claim 30, in which the effective input and output windows are separate elements.

35. A system as in claim 30, in which the cell and beam entry element are integrated to form a continuous construction.

36. A system as in claim 31, in which the first and second electromagnetic beams are characterized by selections from the group consisting of:
   each being of substantially the same wavelength content;
   at least two thereof being of different wave-length content;
   at least one being set to a polarization state;
   at least one being unpolarized;
and the first and second electromagnetic beams are each further characterized by:
   being applied to a sample at the same magnitude oblique angles-of-incidence;
   being applied to a sample at different magnitude oblique angles-of-incidence;
with to respect to said surface.

37. A system for enabling substantially simultaneous investigation of a fluid sample with two electromagnetic radiation beams, said system comprising:
   a. at least one source of a beam electromagnetic radiation;
   b. polarizer means;
   c. optionally compensator means;
   d. fluid sample containing cell;
   e. optionally compensator means;
   f. analyzer means; and
   g. detector means;
wherein said fluid sample containing sample cell comprises:
   effective input and output windows;
   input and output means for entering and exiting fluid sample;
   an internal volume;
said system further comprising a beam entry element in functional combination with said fluid sample containing cell, and being located, as viewed in upright side elevation, below said cell;
such that in use fluid sample is entered to said internal volume of said fluid sample containing cell through said means for entering fluid sample into said fluid sample containing cell, and one electromagnetic radiation beam from said at least one source of a beam electromagnetic radiation is entered through said effective input window of said fluid sample containing cell, and a second electromagnetic radiation beam from said at least one source of a beam electromagnetic radiation is entered through said beam entry element such that said first and second electromagnetic radiation beams both interact with said fluid sample and such that both said first and second electromagnetic radiation beams then enter said detector means.

38. A system for enabling substantially simultaneous investigation of a fluid sample with two electromagnetic radiation beams as in claim 37, wherein said at least one source of a beam electromagnetic is selected from the group consisting of:
- one source of electromagnetic radiation; and
- multiple sources of electromagnetic radiation;

and wherein said detector means is selected from the group consisting of:
- one detector; and
- multiple detectors;

and in which electromagnetic radiation beam(s) which enter said detector means are reflected from said sample.

39. A system for enabling substantially simultaneous investigation of a fluid sample with two electromagnetic radiation beams as in claim 37, wherein a present polarizer and/or compensator and/or analyzer is rotatably mounted and is rotated while data is obtained.

40. A method of quantifying defining parameters of a system comprising a fluid sample on a surface of a two sided stage, comprising the steps of, in either order:

providing an ellipsometer system, and sequentially or simultaneosly obtaining ellipsometric data sets from both first and second sides of system comprising a fluid sample on a surface of a two sided stage;

providing a mathematical model of said fluid sample on a surface of said two sided stage;

then performing a mathematical regression of said mathematical model onto data obtained from said fluid sample on a surface of a two sided stage by a selection from the group consisting of:
- utilizing the data sets obtained from front and back of the fluid sample on a surface of a two sided stage simultaneously;
- utilizing the data sets obtained from front and back of the fluid sample on a surface of a two sided stage independently; and
- utilizing the data sets obtained from front and back of the fluid sample on a surface of a two sided stage both independently and simultaneously.

* * * * *